(12) United States Patent
Cone et al.

(10) Patent No.: US 6,407,831 B1
(45) Date of Patent: Jun. 18, 2002

(54) COHERENT INTERACTION OF OPTICAL RADIATION BEAMS WITH OPTICAL-ELECTRONIC MATERIALS OF GENERALIZED CRYSTAL SYMMETRY

(75) Inventors: Rufus L. Cone, Bozeman, MT (US); Guanrring Wang, Marlborough, MA (US); Yongchen Sun; Randy W. Equall, both of Bozeman, MT (US)

(73) Assignee: Research and Development Institute, Inc., Bozeman, MT (US)

( * ) Notice: Subject to any disclaimer, the term of this patent is extended or adjusted under 35 U.S.C. 154(b) by 0 days.

(21) Appl. No.: 09/463,607

(22) PCT Filed: Jul. 28, 1998

(86) PCT No.: PCT/US98/15724

§ 371 (c)(1),
(2), (4) Date: May 3, 2000

(87) PCT Pub. No.: WO99/05507

PCT Pub. Date: Feb. 4, 1999

Related U.S. Application Data (60) Provisional application No. 60/653,977, filed on Jul. 28, 1997.

(51) Int. Cl.[7] .............................. H01S 4/00; G03H 1/02
(52) U.S. Cl. .............................. 359/7; 359/3; 359/483; 365/119
(58) Field of Search .......................... 359/7, 483, 485, 359/486, 3, 900; 365/119, 106; 372/41, 42

(56) References Cited

U.S. PATENT DOCUMENTS

| | | | | |
|---|---|---|---|---|
| 3,846,764 A | * | 11/1974 | Schneider | 365/119 |
| 3,941,482 A | * | 3/1976 | Schneider | 356/30 |
| 4,038,647 A | * | 7/1977 | Schneider | 359/7 |
| 4,110,004 A | * | 8/1978 | Bocker | 359/485 |
| 4,490,016 A | * | 12/1984 | Schneider et al. | 365/119 |
| 4,807,240 A | | 2/1989 | Goldstone | 372/69 |
| 4,898,436 A | | 2/1990 | Cheng et al. | 359/7 |
| 5,170,268 A | | 12/1992 | Ewbank et al. | 359/7 |
| 5,568,460 A | | 10/1996 | Saikan et al. | 369/100 |
| 5,581,499 A | | 12/1996 | Hamamdijian | 365/106 |
| 5,771,117 A | | 6/1998 | Harris et al. | 359/326 |

* cited by examiner

*Primary Examiner*—Cassandra Spyrou
*Assistant Examiner*—John Juba, Jr.
(74) *Attorney, Agent, or Firm*—McDermott, Will & Emery (57) ABSTRACT

A method for optimizing the interaction of a resonant material having generalized crystal symmetry with a beam or beams of radiation. The invention includes determining a special direction relative to the axes of crystal symmetry of the material and polarizing the interaction radiation beam along this direction. The polarized radiation beam is propagated through the material perpendicular to this special direction. The method and system are used in any application which involves the coherent interaction of optical radiation beams or fields with resonant ion-doped or molecular crystals of various types. Coherent interaction of optical radiation beams or fields with resonant ion-doped or molecular crystals of various types includes the phenomena of optical coherent transients, spectral hole burning, and spatial-spectral holography (also called time and space domain holography) and provides the basis for optical-electronic devices. Such applications include computer and communications networks.

17 Claims, 3 Drawing Sheets

COHERENT INTERACTION OF OPTICAL RADIATION BEAMS WITH OPTICAL-ELECTRONIC MATERIALS OF GENERALIZED CRYSTAL SYMMETRY

REFERENCE TO PRIOR APPLICATIONS

This application claims the benefit of Priority Application Ser. No. 60/653,977, filed Jul. 28, 1997.

BACKGROUND OF THE INVENTION

The present invention relates to the coherent interaction of optical radiation beams with ions or molecules in solids, and to the choice of propagation direction and light polarization relative to the crystal symmetry axes of the solid, and more particularly to optimize the optical-electronic interaction effects in materials with generalized crystal symmetry.

DESCRIPTION OF THE RELATED ART

A variety of optical-electronic applications are based on the coherent interaction of optical radiation beams or fields with ion-doped or molecular crystals of various types; these interactions include optical coherent transients, spectral hole burning, and spatial-spectral holography (also called time- and space-domain holography). Devices based on these concepts are used in optical data storage, real-time optical signal processing, quantum computers, and other coherent computers where the coherent interaction of multiple radiation beams is enhanced, enhanced data erasure in coherent computers, and optical data routing and have applications to computers, communications networks, the Internet and other networks, time delays in RADAR, and numerous other applications.

Natural and synthetic optical materials have a wide range of potential crystal lattice symmetries. (A well-known catalog of all crystal space groups is the International Tables for Crystallography, Edited by Theo Hahn, published by the International Union of Crystallography, D. Reidel Publishing Co.) Within these materials, active ions or molecules occupy crystal 'lattice sites' that can be cataloged into subsets, with members of each subset having identical surroundings and having similar resonant frequencies for coupling to optical radiation (the members of each subset are said to be 'crystallographically-equivalent'); each crystallographically-equivalent subset of lattice sites may contain ions or molecules with a finite number of different spatial orientations. The optical transitions of electrons in the ions or molecules can be described by two quantum energy levels and a transition dipole moment. In general, these transition dipole moments have a plurality of different spatial orientations, according to the different orientations of the crystallographically-equivalent sites noted above. Light beams, on the other hand, must have single optical propagation directions and polarization states relative to the crystal, with the consequence that the light polarization will have a plurality of different spatial relationships with otherwise identical ions or molecules.

When resonant coherent interactions occur, the interaction of the optical field and the two-level quantum systems can be characterized by the optical Rabi frequency:

$$\omega_R = \frac{\bar{p} \cdot \bar{E}_O}{\hbar}$$

where $\bar{p}$ is the electric dipole moment with components $p_i = \langle 1|p_i|2\rangle$ and $\bar{E}_O$ is the optical electric field vector.

(Similar expressions apply for magnetic dipoles and magnetic optical fields. In extreme situations a power-broadened version of the above equation applies.)

The Rabi frequency is determined not, only by the magnitudes of the transition dipole moment and of the optical field, but also by the projection of one onto the other (vector projection or scalar product). Consequently, when arbitrarily polarized radiation is propagated through such materials, the coherent interaction of the field and the crystalline matter will induce macroscopic polarization oscillations at a plurality of different optical Rabi frequencies.

The presence of multiple optical Rabi frequencies generally reduces the effectiveness of the optical-electronic device due to consequent complex transient material polarization behavior and the optical interference or beating of the associated optical signal amplitudes radiated by the material. Such interference, for example, can in turn limit the optical-electronic system bandwidth and hence the response time and data handling capability in the optical-electronic application. The interference may also reduce the optical diffraction efficiency, i.e., the signal selection or deflection efficiency in such devices as optical data routers for optical communications networks and wavelength-division multiplexing systems.

To avoid the deleterious effects of this multiple frequency interference, while still being able to optimize other system parameters, it is necessary to design a procedure for obtaining 'single-Rabi-frequency' behavior in a generalized situation. The small group of materials that have only a single site orientation can readily exhibit single frequency behavior. Here, However, we show that a wider range of materials, including multi-site materials, can exhibit single-Rabi-frequency behavior under the conditions that we have discovered.

The crystalline compound, $Y_3Al_5O_{12}$ (yttrium aluminum garnet—"YAG"), which has been used by several research groups for device demonstrations, is a particularly complicated optical material, and its behavior serves to illustrate the problems arising from the interference effects described above, and also to illustrate our invention. In past applications, light was propagated along the so-called crystallographic <111> direction of YAG, a propagation direction that does not yield single-Rabi-frequency behavior. There are one hundred sixty (160) ions per unit cell of the YAG lattice (the unit cell is the fundamental building block of the crystal). When rare earth ions are substituted as active ions for yttrium at the dodecahedral lattice sites, there are six (6) crystallographically-equivalent sites, each with a differently-oriented local environment. Hence, there are six different directions for the individual transition dipoles of the active rare earth ions. For an arbitrary optical propagation direction and for arbitrary optical polarization, there will be six different Rabi frequencies.

In principle, one could eliminate the degradation in performance arising from the presence of multiple Rabi frequencies by choosing a different material with an appropriately high symmetry that restricts the sites to a single orientation. In general, though, that high-crystal-symmetry approach to obtaining a single Rabi frequency does not work for device applications, since one must simultaneously optimize many other material properties, including the optical coherence or dephasing time, inhomogeneous optical line broadening, transition probability, persistence of spectral hole burning, dependence of all of these properties on the applied magnetic field, and dependence of all of these properties on temperature. Satisfying all of these demands in a single material is at best a difficult challenge, even when no other restrictions on material selection exist (such as the restriction to a single site orientation). This 'high-symmetry' approach has so far proven to be impractical. Conventionally, the optical material had to be chosen from a small subset of available materials, most or all of which do not have a single set of identically-aligned and oriented crystallographically-equivalent dipoles; that represents a sacrifice in potential bandwidth, diffraction efficiency, and performance.

The following example shows the difficulty of the high-symmetry single-site-orientation approach. The choice of a single-site material would make it relatively simple to achieve a single optical Rabi frequency in the transmission of a radiation beam or field, and could thereby increase the effectiveness of the device, but it also significantly reduces the optical transition probability in many cases and even reduces it identically to zero in many cases of interest. It also restricts the choice of materials that may be used to a very small fraction of the totality of optical materials that might be otherwise considered for use in the particular application. Since many interesting optical materials with multiple site orientations have other characteristics that are superior to those of materials with the high crystal symmetry necessary to give a single site orientation, it is advantageous to solve the single Rabi frequency problem in a generalized way, so that optical-electronic devices can benefit from the use of materials with multiple site orientations specifically and from a far wider range of materials generally.

SUMMARY OF THE INVENTION

Accordingly, it is an object of the present invention to provide a technique for eliminating the deleterious effects of multiple Rabi frequencies on the speed and bandwidth characteristics of optical-electronic interaction effects for materials with generalized crystal symmetry.

It is another object of the present invention to provide a technique for reducing material polarization interference in optical-electronic interactions.

It is a further object of the present invention to provide a technique for optimizing optical transition probability in optical-electronic interactions for a wide range of optical materials.

It is a further object of the present invention to provide a technique for optimizing diffraction efficiency in optical-electronic interactions for a wide range of optical materials.

Additional objects, advantages, and novel features of the present invention will become apparent to those skilled in the art from this disclosure, including the following detailed description, as well as by practice of the invention. While the invention is described below with reference to preferred embodiments, it should be understood that the invention is not limited thereto. Those of ordinary skill in the art having access to the teachings herein will recognize additional implementations, modifications, and embodiments, as well as other fields of use, which are within the scope of the invention as disclosed and claimed herein and with respect to which the invention could be of significant utility.

In accordance with the present invention, to reduce undesirable interferences and thereby increase the effectiveness of optical-electronic interactions, a beam of radiation, e.g. a coherent light beam, (or multiple beams of radiation) is propagated through a material having a generalized crystal symmetry with specific light propagation direction and polarization state specified relative to the conventional axes of crystal symmetry of the material (linear or elliptical polarization). Since the material has a generalized crystal symmetry, the material's transition dipoles will have several independent transition directions; that is, the material will have a crystal lattice structure with a plurality of unaligned, differently-orientated dipoles at crystallographically-equivalent sites.

The invention involves a procedure for determining a suitable optical propagation direction and polarization state that projects equally on the respective directions of the transition dipoles, or more typically a subclass of the dipoles, and which is orthogonal to the respective directions of any remaining transition dipoles, i.e. all dipoles of the original subset not within the subclass of dipoles. The radiation beam is polarized, linearly or otherwise, relative to the axes of symmetry to equally project onto each of the dipoles within the subclass of dipoles. Beneficially, the propagating radiation beam is polarized identically with respect to each of the dipoles within the subclass and orthogonally to dipoles outside the subclass of transition dipoles, and accordingly, equally projects onto each of the dipoles within the subclass of transition dipoles.

The propagation of the polarized radiation beam through the material actively excites ions in the subclass of dipoles so as to induce them to oscillate cooperatively. The dipoles of the ions outside the subclass preferably are not oscillated. Advantageously, each of the dipoles in the subclass are oscillated at the substantially same Rabi frequency and have a substantially equal transition intensity.

The relationship of the propagation direction and polarization to the axes of crystal symmetry will change dependent upon the selection of dipoles forming the subclass of dipoles. In any event, the subclass of the dipoles is selected such that there exists a special direction, specified relative to the conventional axes of crystal symmetry, that projects equally on the respective transition dipoles within the subclass and is orthogonal to the respective transition dipoles of the remainder of the dipoles.

According to the invention, a system for propagating a beam of radiation through a material having a plurality of unaligned, differently-orientated crystallographically-equivalent transition dipoles includes a monochromatic frequency-agile radiation emitter (or several emitters) for emitting a beam (or multiple beams) of radiation along a path towards the optical-electronic material. An optical controller or encoder for each beam made up, for example, of an acousto-optical, electro-optical, or other modulator or combination of modulators imposes amplitude or phase information on the beam of radiation (or prepares the beam to manipulate another of the several radiation beams). A possibly-two-dimensional deflector makes adjustments in the beam direction as may be required by the optical-electronic device application. Input optics direct the radiation beam(s) to the crystalline material where the radiation-material interaction critical to device performance occurs. A polarizer is configured (or polarizers are configured) to polarize each emitted radiation beam in a direction such that the radiation beam polarization(s) has (have individually) substantially the same projection with respect to multiple dipoles making up a subclass of transition dipoles. In some cases, the typically very small angles between multiple incident radiation beams can be freely varied while maintaining the desired single Rabi frequency behavior (the garnet example illustrates that); in other cases the small angles typically involved between several beams mean that the conditions can be met simultaneously to a good approximation. Beyond the optical-electronic material, there are output optics and an array of radiation detectors or other independent receiving channels such as optical fibers for the signals.

BRIEF DESCRIPTION OF THE DRAWINGS

The various advantages and merits of the invention will become more apparent as a detailed description of the embodiments thereof is given with reference to the accompanying drawings in which:

FIG. 1 shows the relative orientations of the six orientationally-inequivalent but crystallographically-equivalent docahedral sites in the crystal lattice of $Y_3Al_5O_{12}$. This is a particularly complicated system that has been chosen to illustrate the general procedure that is applicable to any crystalline material (there is a non-denumerable number of possible crystalline materials to which these concepts apply—limits are described below).

DESCRIPTION OF THE INVENTION

Figure 1:
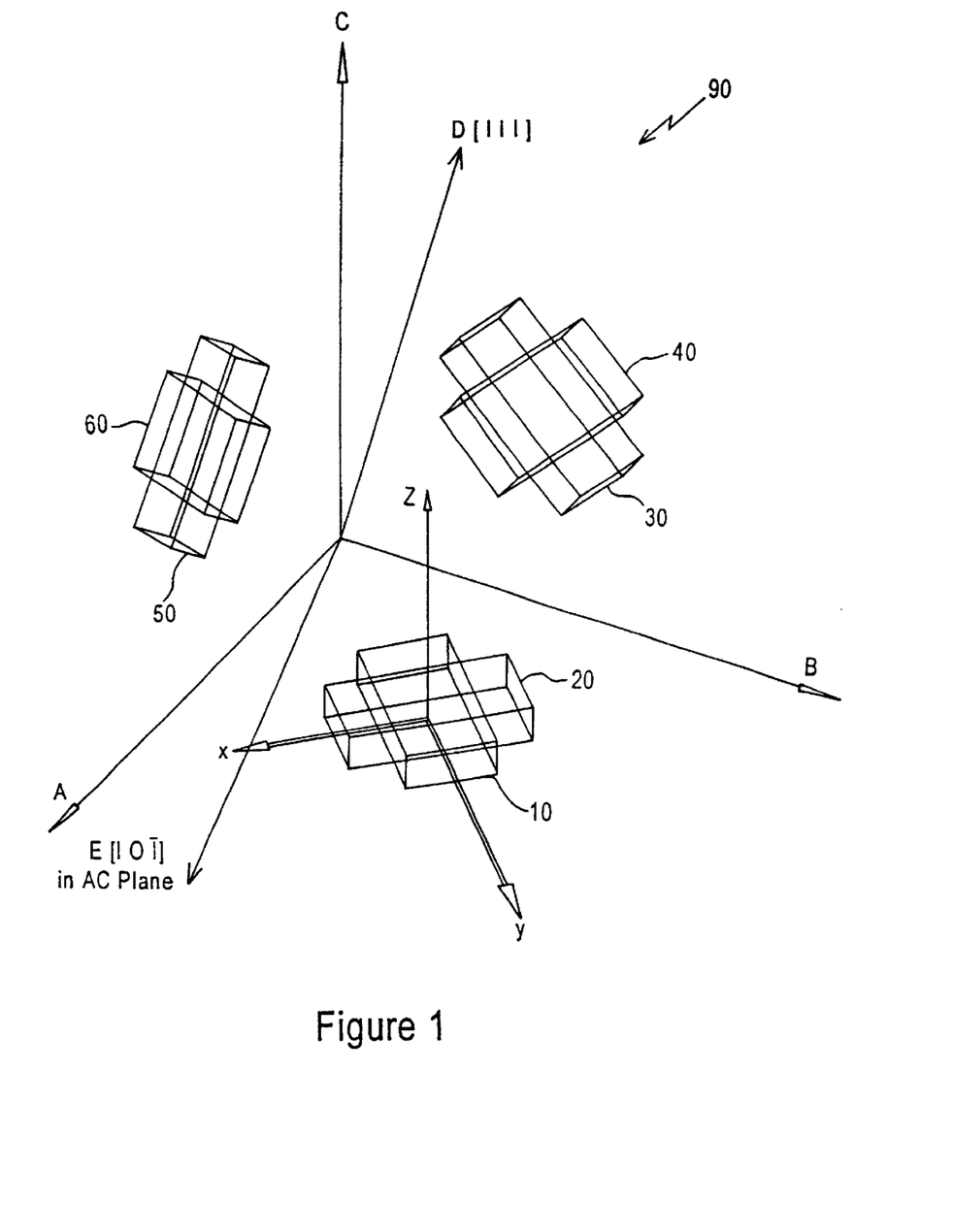

FIG. 1 depicts an optical material 90 having a particularly complicated crystal symmetry. The material 90 is garnet, which serves to illustrate the application of this invention to the symmetry properties of a generalized material, as previously noted in the discussion of the Background Art. The chemical formula for garnet crystals is $A_3B_2C_3O_{12}$. The A ions occupy six crystallographically-equivalent but orientationally-inequivalent versions of this single type of crystallographic site with orientations labeled 10–60, each with dodecahedral point symmetry. The garnet material is doped with rare earth ions which typically substitute for the A ions and experience the same dodecahedral symmetry with respect to the six sites 10–60.

Each of the sites 10–60 has local orthogonal axes, x, y and z, but as the lozenge symbols in FIG. 1 illustrate, these three directions are not equivalent. In FIG. 1, the local axes are shown only for site 10. However, those skilled in the art will recognize that the local axes of each of the sites 10–60 will have a different orientation since, unlike in materials with a single set of identically aligned and oriented crystallographically-equivalent sites, the material 90 has a complicated crystal symmetry and accordingly, differently-oriented, unaligned, but crystallo-graphically-equivalent sites; these six orientations are determined by the so-called $O_h^{10}$ or Ia3d symmetry (standard international crystallographic symbols).

According to convention, the use of the material 90 in optical-electronic devices is not optimum due to the plurality of different orientations of these six sites arising from the garnet crystal symmetry or to another plurality in the generalized case. More particularly, radiation directed through the material 90 in the conventional manner will oscillate ions at the sites 10–60 at six different optical Rabi frequencies which will result in optical interference and transient material polarization behavior such that the effectiveness of the device will be substantially degraded as compared to a device with identically aligned and oriented sites. This optical interference is illustrated by the observed optical nutation shown in FIG. 2 line C.

However, if the Rabi frequencies could be made equal at each of the nutating sites 10–60, the effectiveness of an optical-electronic device incorporating material 90 as the radiation interaction medium, could be substantially improved and the associated transient material polarization behavior simplified. By reducing the optical interference caused by the respective sites 10–60 nutating at different Rabi frequencies, the system bandwidth and diffraction efficiency could be substantially enhanced.

In accordance with the present invention, this can be accomplished by properly selecting the radiation propagation direction and the radiation polarization state specified relative to the conventional axes of crystal symmetry of the material 90.

More particularly, the transition dipoles at each of the sites 10–60 necessarily lie along either the local x, y, or z axes for different sites and electronic states of the material. Hence, when the electric vector of radiation for electric dipole transitions or the magnetic vector for magnetic dipole transitions has a non-zero projection on the dipole, it will induce nutation of the transition dipoles at the sites 10–60.

For an even-electron rare earth ion like $Tm^{3+}$ in the garnet material used for illustration here, the possible electronic states of the material involved in the optical transitions are labeled by conventional symmetry designations $\Gamma_1$, $\Gamma_2$, $\Gamma_3$, and $\Gamma_4$. The symmetry transformation properties of the transition electric dipoles together with the symmetry properties of the two quantum states involved in the transition select either the $p_x$, $p_y$, or $p_z$ dipole corresponding to the local axes shown in FIG. 1. Since the local x, y and z axes of each of the six crystallographically-equivalent sites 10–60 are oriented differently from each other site, six different orientations of dipoles corresponding to the six different sites 10–60 are likewise present.

Hence, if a beam of radiation is directed through the material 90 in the conventional manner, the electric or magnetic field vector will typically have unequal projections with respect to each of the six orientations of transition dipoles. This will necessarily result in unequal transition intensities for each of the sites 10–60 and consequently different Rabi or nutation frequencies. Conventional propagation of the radiation beam along the so-called crystallographic <111> direction forces this multiple Rabi frequency situation to occur.

However, in accordance with the present invention, by properly configuring the beam of radiation transmitted through the material 90, the Rabi or nutation frequencies for at least a subclass of the totality of sites, 10–60 in the present illustration, can be made equal; simultaneously, sites outside the chosen subclass are made inactive. Stated another way, by choosing the proper light propagation direction and light polarization state relative to the axes of crystal symmetry, a cooperative oscillation at a single Rabi frequency can be achieved in the material 90.

Taking the axes of crystal symmetry of the material 90 into consideration, the radiation field direction can be chosen so that all sites being excited by the radiation have the same projection of the radiation field onto the transition dipoles. Hence, whereas the use of conventional techniques in, for example, optical coherent transient applications and spatial-spectral holography, will result in the dipole vectors precessing at different rates under the driving influence of the radiation beam or field thereby causing unwanted cancellations of the material polarization (i.e., the sum of all dipole vectors), by properly choosing the radiation field direction in such applications in accordance with the teachings herein, the dipole vectors will precess at substantially, if not exactly, the same rates when driven by the radiation beam or field and no cancellations of the material polarizations of the precessing dipole vectors will occur.

The proper selection of the radiation field or beam configuration is established by first determining a direction that equally projects on a subclass of the dipoles (corresponding to a subclass of the sites 10–60 for the garnet material case) and which is perpendicular to the remaining dipoles (at the remaining sites 10–60 in the garnet case). This direction has a specific relationship (or perhaps several specific relationships) to the axes of crystal symmetry of the material. The radiation beam is then propagated perpendicular to and polarized along this direction (in the linear polarization case) so as to equally project on the dipole moments.

Thus, the radiation beam or field will be polarized at an equal angle with respect to each of the transition dipoles in the subclass of dipoles that are actively oscillated. The radiation beam or field may be linearly or otherwise polarized, so long as the radiation beam or field equally projects onto the dipoles within the chosen subclass of dipoles. When the electric or magnetic radiation field vector is in the proper direction, the radiation field vector, i.e., the radiation polarization, has the same projection relative to all transition dipoles in the subclass of dipoles and hence identical transition intensities.

Accordingly, for the specific case of the garnet material as indicated in FIG. 1, and for $Tm^{3+}$ ion transitions between states of $\Gamma_1$ and $\Gamma_2$ symmetry, by propagating a radiation beam or field along the A axis (known in the specific garnet case as the 'crystallographic <100> direction') and polarizing the beam or field along the axis B (known in the specific garnet case as the 'crystallographic <010> direction'), the radiation field will induce transitions at identical Rabi frequencies for the four sites 10–40. It will be noted that the four-fold crystal symmetry axis in this case is along axis B. Alternatively, a three-fold crystal symmetry axis lies along axis D of FIG. 1. Accordingly, by propagating a radiation beam or field along axis E and polarizing the beam or field along axis D, the induced transitions for the three sites 10, 40 and 60 will be at identical Rabi frequencies (if the dipole is along y); the other sites are not active.

Figure 2:
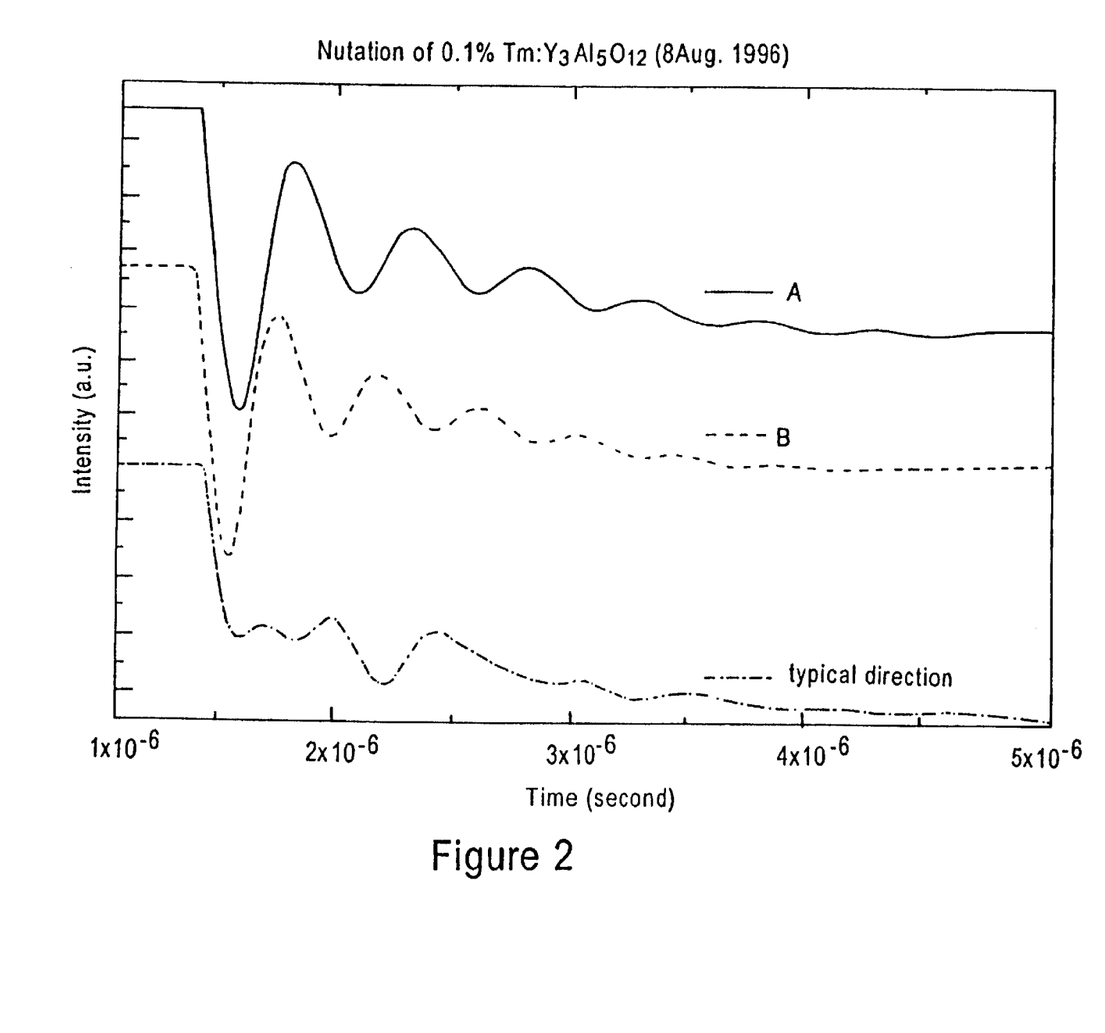
FIG. 2 shows an example of an unoptimized coherent interaction where beating reduces signal amplitude) and shows two different examples, wherein identical optical fields are used, of optimized coherent interaction for the material of FIG. 1.

FIG. 2 depicts the light emission intensities over time caused by propagating and polarizing the radiation beam or field as described above with respect to special directions specified relative to the crystal symmetry axes and corresponding in this case to axis B (line A in FIG. 2) or D (line B in FIG. 2), as depicted in FIG. 1. A third line on the graph depicts the transition intensity over time caused by a conventionally configured radiation beam or field with respect to the crystal lattice structure of material 90 of FIG. 1. FIG. 2 indicates the beneficial effects of the single Rabi frequency behavior resulting from the implementation of the inventive technique described herein.

In each of the above described exemplary applications of the present invention, the dipoles of the sites 10–60 that are actively oscillated exhibit the desired cooperative properties under coherent illumination. In applications utilizing coherent interaction, the above described technique allows optical materials that may have otherwise beneficial properties to be utilized. It should be noted that the above reflects the results of testing carried out on 0.1% $Tm^{3+}$ doped $Y_3Al_5O_{12}$. The $^3H_6(1)$ to $^3H_4(1)$ transition, i.e., 793.374 nm in a vacuum, is an electric dipole transition, and the transition dipole between these states is directed along the local y axis.

Figure 3:
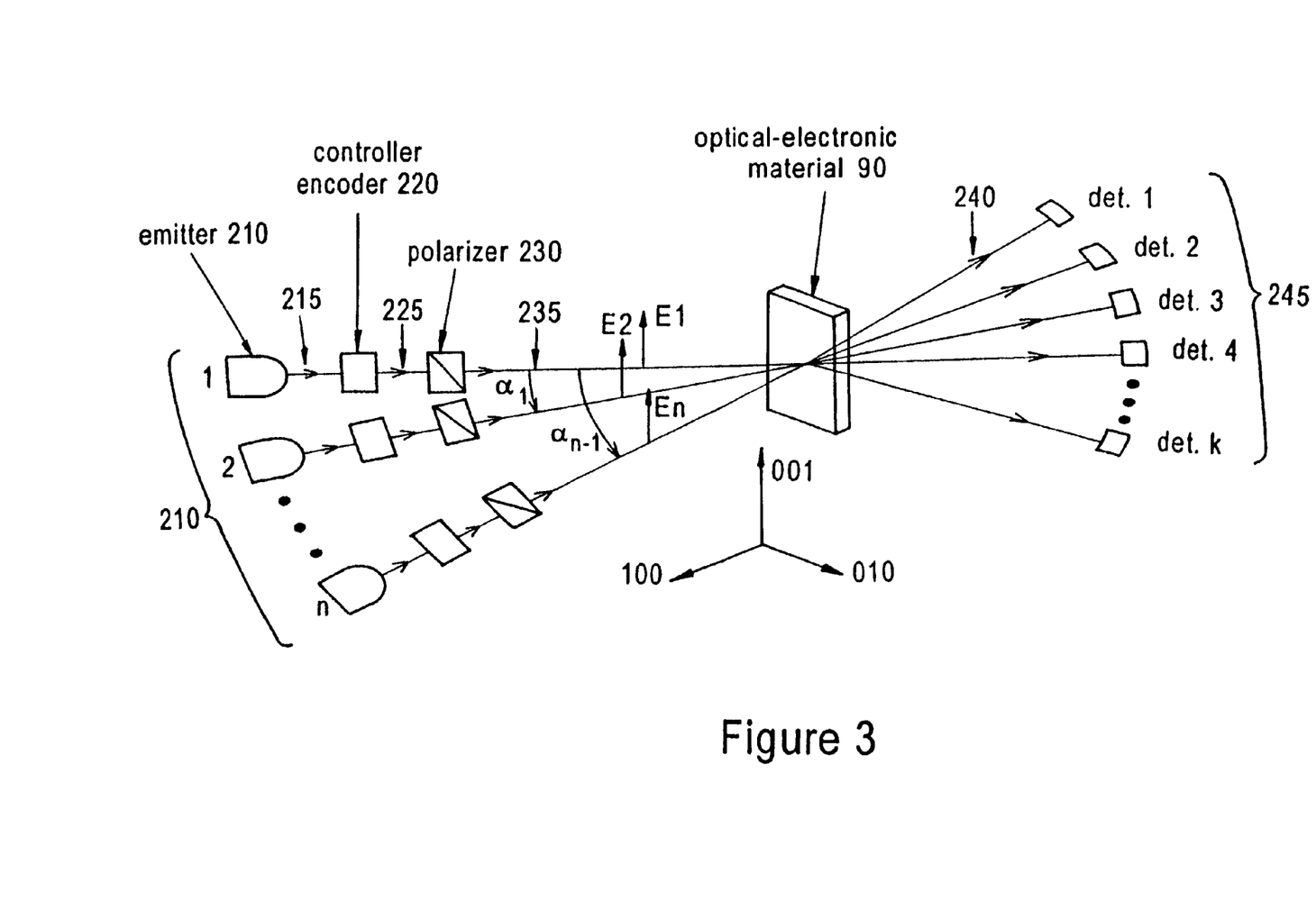
FIG. 3 depicts an optical-electronic device configured to transmit radiation through the generalized optical material in accordance with the optimized material interaction of the present invention.

FIG. 3 depicts a simplified exemplary system configuration in accordance with the present invention. As will be understood by those skilled in the art, the depicted configuration will typically also include other elements such as collimators, lenses, etc., inserted along the radiation beam path as may be desirable for the particular implementation. For the garnet example, the crystal lattice structure of the material 90 includes sites 10–60 as have been described above with reference to FIG. 1.

The system includes a radiation beam emitter 210 (or an array of such emitters) which is shown as a laser source but could be another radiation source as may be suitable for the intended application. The radiation beam 215 emitted from the emitter 210 is propagated in the desired direction by the controller 220 which could, for example, be an acousto-optical modulator (AOM) or other suitable control device for propagating the radiation beam 215 along the proper path with respect to the selected axis of crystal symmetry of the material 90 and modulating its intensity, frequency, and phase. The propagating beam 225 is output from the controller 220 to a polarizer 230 that polarizes the radiation beam with respect to the selected axis of crystal symmetry. The propagating polarized beam 235 is transmitted along the proper path through the material 90.

In the preferred embodiment depicted, and for the illustrative case of the garnet material, the radiation beam is propagated and polarized based upon the axis B of FIG. 1 being the special crystal symmetry direction. The beam 215 emitted by the laser 210 is directed by the controller 220 such that the radiation beam 225 output from controller 220 propagates along a path coinciding with axis A of FIG. 1. The polarizer 230 polarizes the beam such that the output beam 235 is polarized linearly along the axis of crystal symmetry B.

As discussed above, the polarizer 230 polarizes the emitted radiation beam at substantially the same angle with respect to each of the dipoles at the sites 10, 20, 30, and 40, and the controller 220 propagates the radiation beam perpendicular to the direction along which the beam is polarized by polarizer 230. Accordingly, identical Rabi frequencies are induced at sites 10, 20, 30, and 40 with the resultant constructive intensity as indicated in FIG. 2, line A. This result is accomplished even though the material 90 is formed of unaligned, differently oriented crystallographically-equivalent transition dipoles at the sites 10–60. Hence optical interference is substantially reduced, if not eliminated, and transient material polarization behavior is significantly simplified.

As described in detail above, the invention provides a technique for increasing the speed and bandwidth characteristics of optical-electronic transmissions and interactions, reducing material polarization interference in optical-electronic transmissions and interactions, and optimizing optical transition probability in optical-electronic transmissions and interactions through a wide range of optical materials. A highly effective optical system configured to implement the technique is additionally described.

It will also be recognized by those skilled in the art that, while the invention has been described above in terms of only one or more preferred embodiments, it is not limited thereto. The various features and aspects of the above described invention may be used individually or jointly. Further, although the invention may be described in the context of its implementation in a particular environment and for particular purposes, e.g., those skilled in the art will recognize that its usefulness is not limited thereto and that the present invention can be beneficially utilized in any number of environments and implementations. Accordingly, the claims set forth below should be construed in view of the full breath and spirit of the invention as disclosed herein.

The single Rabi frequency direction can be found in Table 1 for all possible crystals. As can be seen from the table, all non-cubic crystals have at least one direction along which all dipoles project equally. For dipoles at sites of higher symmetry, additional directions are given with the same property. For crystals with cubic symmetry, dipoles at site symmetry higher than and including orthorhombic can always project equally onto some axes of the crystal. For sites with even lower symmetry, though, no general solution is given, but it is still possible to find a partial solution for many cases of interest. A partial solution means that a solution exists for some electronic states of the active ions or molecules but not for others. For example, in $Eu:Y_2O_3$, which is a potentially important material in the optical-electronic applications, the $Eu^{3+}$ ion substitutes for $Y^{3+}$ at a $C_2$ site in the cubic crystal (crystal symmetry $T_h$), but the important $Eu^{3+}$ transition $^7F_0$-$^5D_0$ is an electric dipole pointing in the $C_2$ direction and there are several directions in the crystal that project to the dipoles equivalently.

Table 1. A table listing all the single Rabi frequency directions for all crystal symmetries and every possible site symmetry for each crystal symmetry. When there are several possibilities for the same symmetry label, the labels $C_2'$ an $C_2''$ are also used in addition to $C_2$, and $\sigma_d$, $\sigma_v$ are used for the vertical mirror planes in the convention of Koster, Dimmock, Wheeler, and Statz, *Properties of the Thirty-Two Point Groups*, MIT Press, 1963.

| Crystal Classes | Possible Site Symmetries | Conditions | Single Rabi Frequency directions |
|---|---|---|---|
| Triclinic | | | |
| $C_1$ | $C_1$ | | all (all directions work) |
| $C_i$ | $C_i$ | | all |
| | $C_1$ | | |
| Monoclinic | | | |
| $C_2$ | $C_2$ | | all |
| | $C_1$ | | all |
| $C_s(C_{1h})$ | $C_1$ | | $C_2$ axis and a plane* mirror plane and its normal |
| | $C_s$ | | All |
| $C_{2h}$ | $C_1, C_i, C_s$ | | $C_2$ axis and one direction in mirror plane* |
| | $C_2, C_{2h}$ | | all |
| Orthorhombic | | | |
| $D_2$ | $C_1, C_2$ | | 3 major axes |
| | $D_2$ | | all |
| $C_{2v}$ | $C_1, C_2, C_s$ | | 3 major axes |
| | $C_{2v}$ | | all |
| $D_{2h}$ | $C_1, C_2, C_s, C_i, C_{2h}$ | | 3 major axes |
| | $C_{2v}, D_2, D_{2h}$ | | all |
| Tetragonal | | | |
| $C_4$ | $C_1, C_2$ | | $C_4$ axis and 4 directions perpendicular to $C_4$ and 45° from each other* |
| | $C_4$ | | all |
| $S_4$ | $C_1, C_2$ | | $S_4$ axis and 4 directions perpendicular to $S_4$ and 45° from each other* |
| | $S_4$ | | all |
| $C_{4h}$ | $C_1, C_2, C_s, C_{2h}$ | | $C_4$ axis and 4 directions perpendicular to $C_4$ and 45° from each other* |
| | $C_4, S_4, C_{4h}$ | | all |
| $D_4$ | $C_1, C_2$ | | $C_4$ axis |
| | $D_2, C_2', C_2''$ | | $C_4, C_2, C_2$ |
| | $C_4, D_4$ | | all |
| $C_{4v}$ | $C_1, C_2$ | | $C_4$ axis |
| | $C_{2v}, C_s$ | | $C_4$ axis and perpendicular to $C_4$ in the mirror plane |
| | $C_4, C_{4v}$ | | all |
| $D_{2d}$ | $C_1, C_2$ | | $S_4$ axis |
| | $D_2, C_{2v}, C_s, C_2'$ | | $S_4, C_2'$ axes and 2 directions perpendicular to $S_4$ in mirror planes |
| | $S_4, D_{2d}$ | | all |
| $D_{4h}$ | $C_1, C_2, C_i, C_s$ | | $C_4$ axis |
| | $D_2, C_{2h}, C_{2v}, C_2', C_2'', C_5', (\sigma_d, \sigma_v)$ | | $C_4, C_2', C_2''$ |
| | $S_4, C_4, C_{4h}, D_4, C_{4v}, D_{2d}, D_{4h}$ | | all |
| Trigonal | | | |
| $C_3$ | $C_1$ | | $C_3$ axis and 3 directions perpendicular to it (120° apart)* |
| | $C_3$ | | all |
| $C_{3i}$ | $C_1, C_i$ | | $C_3$ axis and 3 directions perpendicular to it (120° apart)* |
| | $C_3, C_{3i}$ | | all |
| $D_3$ | $C_1$ | | $C_3$ axis |
| | $C_2$ | if dipole along $C_2$ | $\perp$ to both the $C_2$ and $C_3$ $C_2$ and $C_3$ axes |
| | | if $\perp$ to $C_2$ | |
| | $C_3, D_3$ | | all |
| $C_{3v}$ | $C_1$ | | $C_3$ axis |
| | $C_s$ | if dipole $\perp$ to mirror plane | 3 direction perpendicular to the $C_{3\ axis\ in}$ the mirror planes $C_3$ and the normals of the mirror planes(3) |
| | | if dipole in the mirror plane | |
| | $C_3, C_{3v}$ | | all |
| $D_{3d}$ | $C_1$ | | $C_3$ axis |
| | $C_2, C_{2h}, C_s$ | if dipoles along $C_2$ axis | perpendicular to $C_3$ in the mirror planes |
| | | if dipole $\perp C_2$ | $C_3$ axis and 3 directions along $C_2$ |
| | $D_3, C_{3v}, D_{3d}$ | | all |
| Hexagonal | | | |
| $C_6$ | $C_3, C_6$ | | all |
| | $C_1, C_2$ | | $C_6$ axis, and 3 directions $\perp$ to $C_6$* |
| $C_{3h}$ | $C_3, C_{3h}$ | | all |
| | $C_1, C_s$ | | $C_3$ axis, and 3 directions $\perp$ to $C_3$* |
| $C_{6h}$ | $C_6, C_{3h}, C_3, C_{6h}, C_{3i}$ | | all |
| | $C_1, C_i, C_2, C_s, C_{2h}$ | | $C_6$ axis, and 3 directions $\perp$ to $C_6$* |

-continued

| Crystal Classes | Possible Site Symmetries | Conditions | Single Rabi Frequency directions |
|---|---|---|---|
| $D_{3h}$ | $C_3, C_{3h}, C_{3v}, D_3, D_{3h}$ | | all |
| | $C_{2v}, C_2, C_s$ | | $C_3$ and 3 $C_2$'s or $C_3$ and 3 directions $\perp$ to $C_{2 \text{ and } C3}$ |
| | $C_1$ | | $C_3$ axis |
| $C_{6v}$ | $C_3, C_{3v}, C_6, C_{6v}$ | | all |
| | $C_{2v}, C_s' (\sigma_d, \sigma_v)$ | | $C_6$ and $\perp \sigma d$, or $\perp \sigma v$ |
| | $C_1, C_2$ | | $C_6$ axis |
| $D_6$ | $C_3, D_3, D_6$ | | all |
| | $D_2, C_2', C_2''$ | | $C_6$ axis and $C_2'$ or $C_2''$ |
| | $C_1, C_2$ | | $C_6$ |
| $D_{6h}$ | $C_3, C_v, C_{3h}, C_{3i}, D_3, C_6, D_{3h}, D_{3d}, C_{6v}, C_{6h}, D_6$ | | all |
| | $D_2, D_{2h}, C_{2v}, C_2', C_2''$ | | $C_6$ and $C_2'$ or $C_2''$ |
| | $C_{2h}(C_2 \text{ axis of } C_{2h} C_6 \text{ axis})$ $Cs' (94_d, 94_v)$ | | |
| | $C_1, C_i, C_s, C_2, C_{2h}$ | | $C_6$ axis |
| Cubic | | | |
| T | $C_1, C_2$ | if dipoles along $C_2$ | $C_2$ and $C_3$ axes |
| | $C_3$ | | $C_2$ axes |
| | $D_2$ | | $C_3$ and $C_2$ axes |
| | T | | all |
| $T_h$ | $T, T_h$ | | all |
| | $C_3, C_{3i}$ | | $C_2$ |
| | $D_{2h}, D_2, C_{2v}$ | | $C_2$ and $C_3$ |
| | $C_1, C_i, C_s, C_2, C_{2h}$ | if dipoles along $C_2$ | $C_2, C_3$ and $\perp C_2$ in mirror plane |
| Td | $T, Td$ | | all |
| | $C_3, C_{3v}$ | | $S_4$ |
| | $D_{2d}, S_4$ | | $S_4, C_3$, and $\perp S_4$ in mirror plane |
| | $D_2, C_{2v}$ | | $S_4, C_3$ |
| | $C_1, C_2, C_s$ | if dipoles along $S_4$ or $\perp$ to the mirror planes | $S_4, C_3$ |
| O | T, O | | all |
| | $C_3, D_3$ | | $C_4$ |
| | $D_4, C_4$ | | $C_4, C_3, C_2'$ |
| | $D_2$ | | $C_4, C_3$ |
| | $C_1, C_2$ | if dipoles along $C_4$ | $C_4, C_3, C_2'$ |
| | | if dipoles along $C_2'$ | $C_4, C_3$ |
| $O_h$ | $T, T_h, T_d, O, O_h$ | | all |
| | $C_3, C_{3i}, C_{3v}, D_3, D_{3d}$ | $C_4$ | |
| | $D_4, C_{4v}, D_{2d}, D_{4h}, C_4, S_4, C_{4h}$ | | $C_4$ and $C_3$ and $C_2'$ |
| | $D_2, C_{2v}, D_{2h}$ | | $C_4$ and $C_3$ |
| | $C_1, C_2, C_s$ | if dipoles along $C_4$ | $C_4$ and $C_3$ and $C_2'$ |
| | $C_i, C_{2h}$ | if dipoles along $C_2'$ | $C_4$ and $C_3$ |

*Such a plane or direction exists but has to be determined experimentally.

As will be appreciated, an important aspect of the invention resides in optimizing the coupling of the radiation to the dipoles of the optical material. This coupling eventually results in changes to the material (for example in optical data storage applications) and changes in the radiation beams (for example in signal processing applications or in readout of stored information). As noted above this coupling is called the "coherent interaction of optical radiation beams or fields with ion doped or molecular crystals of various types". The direction of propagation is used to optimize that coupling. The dipoles represent, model, or describe the nature of a bulk material. The optimization of coupling is the key idea. "Propagation" becomes important as it affects this coupling.

Thus, the principles of the invention are applicable in any optical-electronic application which is based on the coherent interaction of optical radiation beams or fields with ion-doped or molecular crystals. Devices which use the concepts include optical data storage, real-time optical signal processing, quantum computers, coherent computers, and optical data routing.

The invention has been described with reference to certain preferred embodiments. However as obvious variations thereon will become obvious to those skilled in the art, the invention is not to be considered as limited thereto.

What is claimed is:

1. A method for propagating a beam of radiation through a material having generalized crystal symmetry, comprising the steps of:

determining a direction D, said direction D being a direction at which radiation equally projects on a subclass of transition dipoles and is perpendicular to dipoles not contained in the subclass, said direction D having a specific relationship to the axes of crystal symmetry of the material;

polarizing the radiation beam along the direction D; and propagating the polarized radiation beam perpendicular to the direction D, wherein the polarized radiation beam is polarized at substantially equal angles with respect to each transition dipole of said subclass, has substantially the same projection relative to all transition dipoles in said subclass, and creates substantially identical transition intensities in and coherent transient responses from each transition dipole of said subclass, and substantially no response from dipoles not contained in the subclass.

2. A method according to claim 1, wherein the radiation beam is coherent.

3. A method according to claim 1, wherein the radiation beam is linearly polarized or elliptically polarized.

4. A method according to claim 1, wherein the propagation of the polarized radiation beam through the material actively excites ions in the subclass of transition dipoles to cooperatively oscillate.

5. A method according to claim 1, wherein the propagation of the polarized radiation beam through the material actively oscillates ions in the subclass of transition dipoles at substantially the same Rabi frequency.

6. A method according to claim 1, wherein the material includes a crystal lattice structure having a plurality of unaligned, differently oriented crystallographically-equivalent transition dipoles.

7. A method according to claim 1, wherein said method is conducted in a device for optical data storage, real-time optical signal processing, or optical data routing.

8. A method according to claim 1, wherein said method is conducted in combination with a computer, communications network, or radar.

9. A method for propagating at least one beam of radiation through a material having a crystal lattice structure with a plurality of unaligned, differently oriented crystallographically-equivalent transition dipoles, comprising the steps of:

propagating the radiation beam;

encoding information onto the beam;

directing the propagating radiation beam towards the material at an angle so that propagation within the crystal is perpendicular to a direction D, the direction D being a direction in which radiation equally projects on a subclass of transition dipoles and is perpendicular to transition dipoles not contained in the subclass, said direction D having a specific relationship to the axes of crystal symmetry of the material; and polarizing the propagating radiation beam substantially in direction D, wherein the polarized radiation beam is polarized at substantially equal angles with respect to each transition dipole of said subclass, has substantially the same projection relative to all transition dipoles in said subclass, and creates substantially identical transition intensities in and coherent transient responses from each transition dipole of said subclass, and substantially no response from dipoles not contained in the subclass.

10. A method according to claim 9, wherein the propagation of the polarized radiation beam through the material causes excited ions in the multiple transition dipoles to actively and cooperatively oscillate.

11. A method according to claim 9, wherein the propagation of the polarized radiation beam through the material actively oscillates the multiple transition dipoles at a substantially equal Rabi frequency.

12. A system for propagating a beam of radiation through a material having a plurality of unaligned, differently oriented, crystallographically-equivalent transition dipoles, comprising:

a radiation emitter for emitting a beam of radiation;

a controller for controlling the beam of radiation to propagate in a direction perpendicular to a direction D, said direction D being a direction at which radiation equally projects on a subclass of transition dipoles and is perpendicular to transition dipoles not contained in the subclass, said direction D having a specific relationship to the axes of crystal symmetry of the material; and a polarizer for polarizing the emitted radiation beam along the direction D;

wherein, said subclass of transition dipoles includes a plurality of transition dipoles, and the polarized radiation beam is polarized at substantially equal angles with respect to each transition dipole of said subclass, has substantially the same projection relative to all transition dipoles in said subclass, and creates substantially identical transition intensities in and coherent transient responses from each transition dipole of said subclass, and substantially no response from dipoles not contained in the subclass.

13. A system according to claim 12, wherein the radiation beam is polarized along a direction and further comprising:

a controller for propagating the radiation beam perpendicular to said direction.

14. A system according to claim 12, wherein said system is used in combination with a device for optical data storage, real-time optical signal processing, or optical data routing.

15. A system according to claim 12, wherein said system is used in combination with a computer, communications network or radar.

16. The system according to claim 12, wherein said controller includes a modulator.

17. The system according to claim 16, wherein said modulator modulates the intensity, frequency and phase of said beam of radiation.

* * * * *

UNITED STATES PATENT AND TRADEMARK OFFICE
CERTIFICATE OF CORRECTION

PATENT NO. : 6,407,831 B1
DATED : June 18, 2002
INVENTOR(S) : Cone et al.

It is certified that error appears in the above-identified patent and that said Letters Patent is hereby corrected as shown below:

Title page,
Item [75], Inventors, second named inventor, "Guanrring Wang" with
-- Guangming Wang --.

Column 1,
Line 9, please insert after the "Reference to Prior Applications" section and before the "Background of the Invention" section, -- GOVERNMENT SUPPORT
This invention was made with government support under grant number F49620-00-1-0314 awarded by the United States Air Force (USAF/AFOSR). The government has certain rights in the invention. --

Signed and Sealed this

Tenth Day of August, 2004

JON W. DUDAS
*Acting Director of the United States Patent and Trademark Office*